(12) United States Patent
Serna

(10) Patent No.: US 10,792,389 B2
(45) Date of Patent: Oct. 6, 2020

(54) ENZYME DEGRADABLE SYSTEM FOR UNDERGARMENTS AND FEMININE HYGIENE ARTICLES

(71) Applicant: Rochelle Serna, San Pedro, CA (US)

(72) Inventor: Rochelle Serna, San Pedro, CA (US)

( * ) Notice: Subject to any disclaimer, the term of this patent is extended or adjusted under 35 U.S.C. 154(b) by 447 days.

(21) Appl. No.: 15/783,805

(22) Filed: Oct. 13, 2017

(65) Prior Publication Data

US 2019/0111176 A1  Apr. 18, 2019

(51) Int. Cl.

| | | |
|---|---|---|
| *A61F 13/53* | (2006.01) | |
| *A61F 13/84* | (2006.01) | |
| *A61L 15/62* | (2006.01) | |
| *A61F 13/15* | (2006.01) | |
| *A61F 13/539* | (2006.01) | |
| *A61L 15/22* | (2006.01) | |

(Continued)

(52) U.S. Cl.
CPC ......... *A61L 15/62* (2013.01); *A61F 13/15211* (2013.01); *A61F 13/15252* (2013.01); *A61F 13/539* (2013.01); *A61F 13/84* (2013.01); *A61L 15/225* (2013.01); *A61L 15/38* (2013.01); *A61L 15/60* (2013.01); *C12Y 302/01004* (2013.01); *A61F 2013/530029* (2013.01); *A61F 2013/530233* (2013.01); *A61F 2013/530343* (2013.01); *A61F 2013/530386* (2013.01); *A61F 2013/530481* (2013.01)

(58) Field of Classification Search
CPC .......... A61F 13/15211; A61F 13/15252; A61F 2013/15235; A61F 2013/15261; A61F 2013/530029; A61F 2013/530197; A61F 2013/530313; A61F 2013/530481; A61F 2013/530795; A61F 2013/5381; A61F 2013/8438; A61F 2013/53481; A61L 15/36; A61L 15/38; A61L 15/62
See application file for complete search history.

(56) References Cited

U.S. PATENT DOCUMENTS

| | | | | |
|---|---|---|---|---|
| 4,944,734 A | * | 7/1990 | Wallach | ................. A61F 13/537 |
| | | | | 604/358 |
| 5,049,395 A | * | 9/1991 | Chang | ................ A61F 13/15252 |
| | | | | 424/473 |

(Continued)

*Primary Examiner* — Catharine L Anderson
(74) *Attorney, Agent, or Firm* — Trestle Law, APC; Maymanat S. Afshar

(57) ABSTRACT

An enzyme-degradable system for undergarments and feminine hygiene articles works to decompose the undergarments and feminine hygiene articles upon being triggered by bodily fluids, such as urine. The undergarment or feminine hygiene article comprises an absorbent core, an inner sheet of biodegradable material, and an outer sheet of biodegradable material. The core includes at least one of the following: a cellulose material, a wood pulp, a biodegradable and bioactive thermoplastic aliphatic polyester derived from renewable resources (polylactic acid plastic—PLA), and a superabsorbent polymer (SAP). The inner and outer sheets comprise a plant based cellulosic nonwoven material. The cellulase enzyme decomposes the absorbent core, the inner sheet, and the outer sheet upon contact with a bodily fluid. The cellulase enzyme may include DIS-1018 Cellulose-AN, a pH buffer, and additives. Fasteners made from a resilient, biodegradable material help secure the undergarments and feminine hygiene articles to the body.

14 Claims, 2 Drawing Sheets

200

Table 1. Proposed variable ranges of key factors.

| | Factor | Levels |
|---|---|---|
| 202 | Enzyme 1 (w/w%) | 0.2-1 |
| 204 | Enzyme 2 (w/w%) | 0.2-1 |
| 206 | Enzyme 3 (w/w%) | 0.2-1 |
| 208 | Adhesive remover (w/w%) | 0.1-0.5 |
| 210 | pH | 6-7 |
| 212 | Reaction time (hr) | 8-48 |
| 214 | Buffer (%) | 0.1-0.5 |

(51) Int. Cl.
*A61L 15/38* (2006.01)
*A61L 15/60* (2006.01)

(56) References Cited

U.S. PATENT DOCUMENTS

| | | | | |
|---|---|---|---|---|
| 5,073,202 | A | * 12/1991 | Wallach | A61F 13/15252 134/42 |
| 5,234,915 | A | * 8/1993 | Mathur | A61F 13/15252 514/449 |
| 8,227,059 | B2 | * 7/2012 | Sato | A61F 5/445 428/35.2 |
| 2008/0200890 | A1 | * 8/2008 | Wood | A01N 25/10 604/360 |

* cited by examiner

200

Table 1. Proposed variable ranges of key factors.

| Factor | Levels |
|---|---|
| 202 Enzyme 1 (w/w%) | 0.2-1 |
| 204 Enzyme 2 (w/w%) | 0.2-1 |
| 206 Enzyme 3 (w/w%) | 0.2-1 |
| 208 Adhesive remover (w/w%) | 0.1-0.5 |
| 210 pH | 6-7 |
| 212 Reaction time (hr) | 8-48 |
| 214 Buffer (%) | 0.1-0.5 |

ENZYME DEGRADABLE SYSTEM FOR UNDERGARMENTS AND FEMININE HYGIENE ARTICLES

FIELD OF THE INVENTION

The present invention relates generally to an enzyme-degradable system for undergarments and feminine hygiene articles. More so, the present invention relates to an enzyme-degradable system provides a formulation of cellulase enzymes, a blend of enzymes, and other biodegradable ingredients that are integrated into disposable undergarments and feminine hygiene articles; whereby the cellulase enzymes work to decompose the absorbent core and inner and outer sheets of the undergarments and feminine hygiene articles upon being triggered by bodily fluids, such as urine.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

It is known in the art that disposable diapers are so popular, that they present a pollution problem. There is considerable concern that disposable diapers, when placed in domestic garbage or landfill, represent an environmental hazard. In addition to the obvious problems of human waste the materials used in the diapers are durable and become part of the environment. As these materials are chemical-plastics they are not a welcome part of the environment and cannot be removed by natural means.

Often, females are faced with the challenge of disposing of used feminine hygiene articles, such as tampons, sanitary napkins and the like. A typical method of disposal in public restrooms and the like involves wrapping the used sanitary napkin or tampon in an awkward bundle of toilet paper. This, however, does not provide a secure wrapping of the article, thus creating an unsanitary and messy package. It is known that female hygiene particles are fabricated from plastic, so as to create a fluid resistant container. However, plastics represent a large environmental concern, as most plastics are non-biodegradable, and the purpose of this particular bag is disposal.

Generally, environmental concerns have suggested a need for materials having polymer-like properties but without the degree of permanence typically associated with synthetic polymers. The decreasing availability of landfill space, as well as the increased costs of municipal solid waste disposal, have put increasing emphasis on minimizing the impact of nondegradable materials, including synthetic polymers, on the solid waste stream. Man-made polymers are typically not readily degraded by microorganisms that degrade most other forms of organic matter and return them to the biological life cycle.

It is known that cellulosic materials are generally defined as those materials which contain cellulose. Cellulose is generally defined as a polymer of -D-glucose units. There are new strains of bacteria with genetically enhanced capabilities need to be produced to degrade and break down cellulase materials and thereby make the cellulase more environmentally and commercially feasible.

Other proposals have involved biodegradable diapers and tampons, and disposing thereof. The problem with such biodegradable articles is that they do not break down upon contact with urine because of their chemical composition. The material composition is not, for example, cellulase-based, or integrated with enzymes, to expedite the degradation process. Even though the above cited biodegradable diapers and tampons meets some of the needs of the market, a formulation of cellulase enzymes and other biodegradable ingredients that are integrated into disposable undergarments and feminine hygiene articles; whereby the cellulase enzymes work to decompose the absorbent core, and inner and outer sheets, and fasteners of the undergarments and feminine hygiene articles upon being triggered by urine, is still desired.

SUMMARY

Illustrative embodiments of the disclosure are generally directed to an enzyme-degradable system for undergarments and feminine hygiene articles. The enzyme-degradable system provides a formulation of cellulase enzymes comprising a cellulose, a blend of enzymes, and other biodegradable ingredients that are integrated into disposable undergarments and feminine hygiene articles. The cellulase enzyme works to decompose the undergarments and feminine hygiene articles upon being triggered by bodily fluids. In one embodiment, the cellulase enzyme is DIS-1018 Cellulose-AN.

In one embodiment, the enzyme-degradable system for an undergarment or a feminine hygiene article comprising an undergarment or feminine hygiene article having an absorbent core, an inner sheet of biodegradable material, and an outer sheet of biodegradable material, the core including at least one of the following: a cellulose material, a wood pulp, a biodegradable and bioactive thermoplastic aliphatic polyester derived from renewable resources (polylactic acid plastic—PLA), and a superabsorbent polymer (SAP), the inner and outer sheets comprising a plant based cellulosic nonwoven material.

In some embodiments, the system further comprises at least one cellulase enzyme that integrates into the absorbent core, or the inner and outer sheets, or both. The cellulase enzyme is configured to help decompose the absorbent core, the inner sheet, and the outer sheet upon contact with a bodily fluid. The undergarment or feminine hygiene article may further include at least one fastener at a peripheral region of the undergarment. The fastener may comprise a resilient, biodegradable material that is degradable by the cellulase enzyme.

One objective of the present invention is to decompose an undergarment or feminine hygiene article upon contact with urine.

Another objective is to provide a decomposable diaper or undergarment.

Yet another objective is to reduce waste in landfills by integrating cellulase enzymes into the diapers and tampons.

Yet another objective is to provide a resilient, biodegradable fastener, such as a waist strips at each end of the undergarment to facilitate the fit of the undergarment.

Yet another objective is to initiate break down of the undergarment upon urination engaging the inner or outer layers.

Yet another objective is to provide an inexpensive to manufacture an enzyme-degradable system for an undergarment or a feminine hygiene article.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

Figure 1:
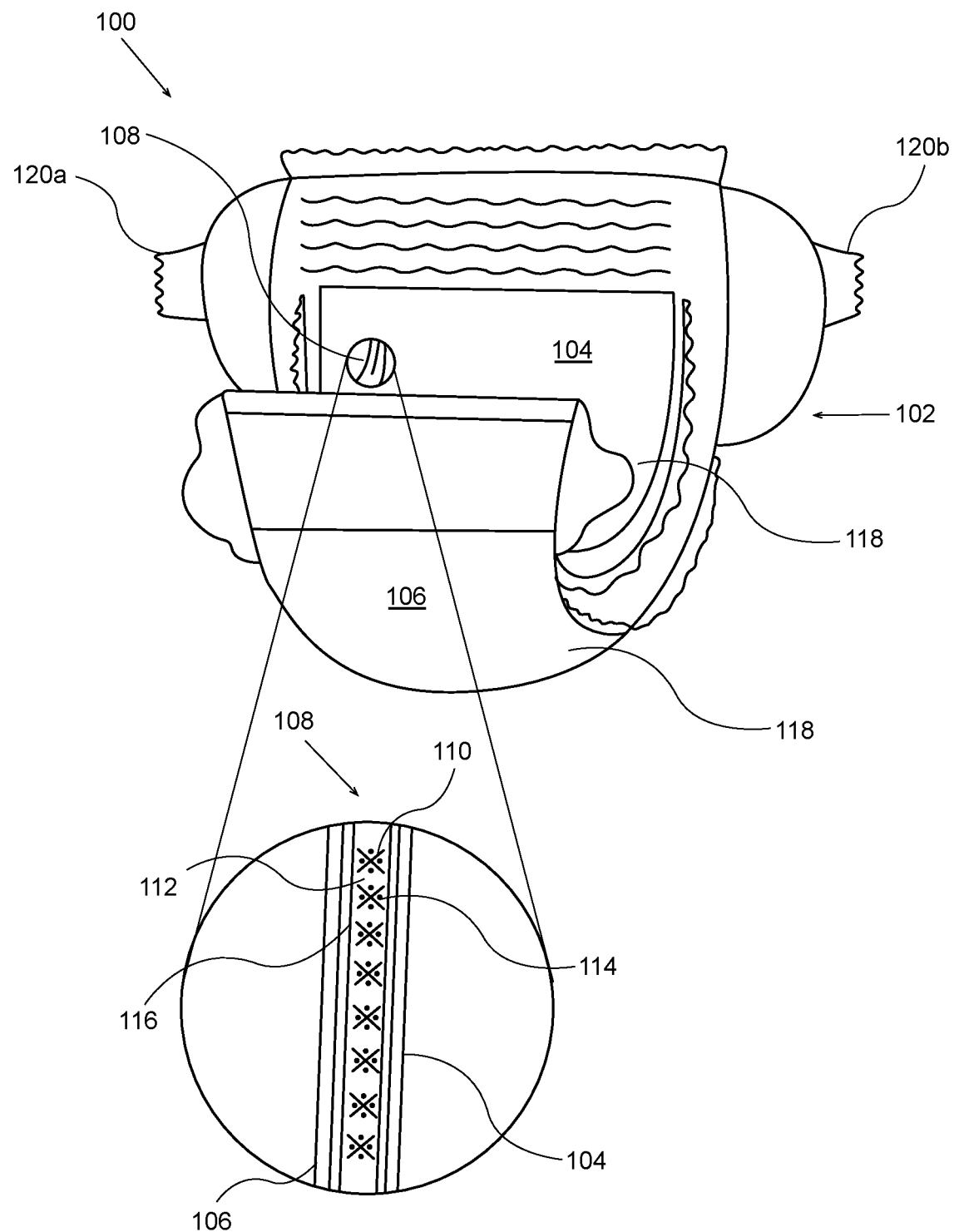
FIG. 1 illustrates a blow up view of an exemplary enzyme-degradable system for undergarments and feminine hygiene articles, in accordance with an embodiment of the present invention.
Figure 2:
FIG. 2 illustrates a Table of an exemplary cellulase enzyme and properties thereof, in accordance with an embodiment of the present invention.

An enzyme-degradable system 100 for undergarments and feminine hygiene articles is referenced in FIGS. 1-2. The enzyme-degradable system 100 for undergarments and feminine hygiene articles, hereafter "system 100" provides an undergarment or a feminine hygiene article 102 that has integrated therein a cellulose construction that is configured for degradation by at least one cellulase enzyme 202, 204, 206, or blend of enzymes. The cellulase enzyme 202, 204, 206 integrates into the components of the undergarment or a feminine hygiene article 102 to help decompose the absorbent core 108, and inner and outer sheets 104, 106.

In one non-limiting embodiment, the undergarment may include, without limitation, a disposable baby diaper, a disposable adult diaper, underwear, and a pair of shorts. The feminine hygiene article may include, without limitation, a tampon, a sanitary napkin, and a menstrual pad. Either the undergarment or the feminine hygiene article is operable with the system 100.

As referenced in FIG. 1, the undergarment and the feminine hygiene article 102 includes an absorbent core 108, an inner sheet 104 of biodegradable material, and an outer sheet 106 of biodegradable material. The absorbent core 108 provides the greatest absorption for the undergarment or the feminine hygiene article 102.

In one embodiment, the absorbent core 108 includes at least one of the following: a cellulose material 110, a wood pulp 112, a biodegradable and bioactive thermoplastic aliphatic polyester 114 derived from renewable resources (polylactic acid plastic—PLA), and a superabsorbent polymer 116 (SAP). In one other embodiment, the fluff pulp, SAP, and or other elements of the core 108 may also be recycled or reclaimed.

In some embodiments, the absorbent core 108 may further include a cotton pulp. The superabsorbent polymer of the absorbent core 108 may be starch based. The thermoplastic aliphatic polyester 114 of the absorbent core 108 may be biodegradable, bioactive, and derived from renewable resources. Further, the absorbent core 108 is a nonwoven material to restrict leakage of bodily fluids.

The inner sheet 104 engages the body of the wearer, while the outer sheet 106 faces opposite the body. Both sheets 104, 106 sandwich the absorbent core 108, with a peripheral region 118 of the sheets 104, 106 sealing together to hold the core 108 in place, and prevent seepage of bodily fluids from the absorbent core 108 outwardly.

In some embodiments, the inner and outer sheets 104, 106 are fabricated from a plant based cellulosic, and nonwoven material. In other embodiments, the sheets 104, 106 are fabricated from a nonwoven material. In other embodiments, the inner and outer sheets 104, 106 may be fabricated from a polymer blend nonwoven, like PLA, or recycled or reclaimed nonwoven material that is partially cellulose based. The material may also be reclaimed.

Those skilled in the art will recognize that such cellulose materials, such as make up the core 108 and sheets 104, 106 are more easily degradable than standard chemical based polymers. Thus, the present disclosure differs from the prior art undergarment and feminine hygiene article in that it utilizes a lower concentration of chemical plastic and polymers.

In one non-limiting embodiments, the undergarment or feminine hygiene article 102 may further include at least one fastener 120a, 120b that is disposed at a peripheral region 118 of the sheets 104, 106 of the undergarment or feminine hygiene article. The fastener 120a, 120b works to help secure the undergarment or feminine hygiene article to the body; including wrapping around the thighs, legs, hips, and pubic regions of the body. The fastener 120a, 120b may include a resilient, biodegradable material that may be degradable by the cellulase enzyme 202, 204, 206. In one embodiment, the fastener 120a, 120b is an adhesive tab. Though other fastening mechanisms known in the art of undergarments and feminine hygiene articles may be used.

Turning now to Table 200 of FIG. 2, the system 100 provides at least one cellulase enzyme 202, 204, 206, or blend of enzymes, that is integrated into the absorbent core 108, or the sheets 104, 106, or both. The cellulase 202, 204, 206 helps to at least partially decompose at least one of: the absorbent core 108, the inner sheet 104, and the outer sheet 106 upon contact with a bodily fluid.

In other embodiments, the cellulase enzyme 202, 204, 206 may help to decompose trash fills. It is significant to note that enzyme degradation helps solve the problem that landfills present to biodegradable products. Those skilled in the art will recognize that biodegradable products require air to degrade, whereas landfills are an anaerobic environment. Enzymes, however, degrade the product with the trigger of liquid, not air so integrating the cellulase enzyme into the undergarment or feminine hygiene article helps solves this issue in any condition.

The cellulase enzyme 202 may include, without limitation, a DIS-1018 cellulose-AN. Though any number of cellulase enzymes that are actuated upon contact with bodily fluids, such as urine, may be used.

Looking again at Table 200, the system 100 provides at least one cellulase enzyme 202, 204, 206 that is triggered by bodily fluids, such as urine, to breakdown the cellulase materials of the absorbent core 108, and inner and outer sheets 104, 106. In one embodiment, the cellulase enzyme 202 is DIS-1018 Cellulose-AN a hydrolyzing enzyme. Though different variations of the cellulase enzyme may be used.

In another embodiment, the cellulase enzyme 202, or blend of enzymes, can compose 10% to 100% of the product weight. The cellulase enzyme 202 or blend of enzymes may be selected from cellulases, amylases, pectinases, and other enzymes with an Enzyme Committee number from EC 3.2.1.1 to EC 3.2.1.203, especially cellulases, more especially *Aspergillus niger* cellulases with activity of 10,000-500,000 units per gram in a solid form or 10,000-500,000 units per gram in a liquid form.

Table 200 shows an exemplary first cellulase enzyme 202. As discussed above, the bodily fluid, such as an acidic urine, triggers the cellulase enzyme 202 to begin decomposing the core 108 and sheets of the undergarment and feminine hygiene article.

In one non-limiting embodiment, the cellulase enzyme 202 has a proposed variable range between 0.2 to 0.1 percent. Though in other embodiments, a slightly different second cellulase enzyme 204 has a proposed variable range between 0.2 to 0.1 percent. A third cellulase enzyme 206 has a proposed variable range between 0.2 to 0.1 percent. As discussed above, at least one fastener 120a, 120b helps secure the undergarment and the feminine hygiene article to the body. An adhesive remover 208 to be used with the fastener has a variable range between 0.1 to 0.5 percent.

In some embodiments, the cellulase enzyme 202 may include a pH buffer 210 having a pH ranging from 6 to 7. Because of the acidity of urine, such a pH buffer may be required to neutralize the urine. At this pH concentration range, a reaction time 212 to begin decomposing the cellulase materials of the core 108 and sheets may be between about 8-48 hours. The buffer percentage 214 for this decomposition is from 0.1 to 0.5 percent.

In one embodiment, the pH buffer 210 comprises 0.01-10% of the product weight and result a pH value of 5.5-9.0 when dissolved in water, human urine, or human blood. In some embodiments, the pH buffer 210 may be selected from at least one of the following: inorganic phosphates, diphosphates, triphosphates, pyrophosphates, organic phosphonates and polycarboxylic acids, especially in their salts with sodium, potassium, calcium, and)- alanine (MGDA), and N,N-bis(carboxymethyl)-glutamic acid (GLDA).

In another embodiment, the cellulase enzyme 202 comprises at least one additive. The at least one additive may be composed of 0.001-5% of the product weight. The at least one additive may include at least one of the following: adhesive removers, preservatives, glycerol, polyethylene glycol, alcohols with 2-8 carbons, sugars with 3-8 carbons, and sugar alcohols with 3-8 carbons.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. An enzyme-degradable system for an undergarment and a feminine hygiene article, the system comprising:
    an absorbent core, the core including at least one of the following: a cellulose, a wood pulp, a thermoplastic aliphatic polyester, and a superabsorbent polymer;
    an inner sheet comprising a plant based cellulosic nonwoven material;
    an outer sheet comprising the plant based cellulosic nonwoven material; and
    a cellulase enzyme being integrated into the absorbent core, or the sheets, or both, the cellulase enzyme helping to at least partially decompose at least one of: the absorbent core, the inner sheet, and the outer sheet upon contact with a bodily fluid,
        wherein the cellulase enzyme comprises *Aspergillus niger* cellulase having an activity of 10,000-500,000 units per gram in a solid form or 10,000-500,000 units per gram in a liquid form.

2. The enzyme-degradable system of claim 1, wherein the cellulase enzyme comprises a pH buffer, the pH buffer including at least one of the following: inorganic phosphates, diphosphates, triphosphates, pyrophosphates, organic phosphonates and polycarboxylic acids, salts of sodium, potassium, calcium, sodium phosphate, sodium triphosphate, Alanine, N,N-bis(carboxymethyl)-alanine, and N,N-bis(carboxymethyl)-glutamic acid.

3. The enzyme-degradable system of claim 1, wherein the cellulase enzyme comprises at least one additive, selected from: an adhesive removers, a preservative, glycerol, polyethylene glycol, an alcohol having 2-8 carbons, a sugar having 3-8 carbons, and a sugar alcohol having 3-8 carbons.

4. The enzyme-degradable system of claim 1, wherein the inner and outer sheets comprise a biodegradable material.

5. The enzyme-degradable system of claim 1, wherein said absorbent core is fabricated from a cellulosic nonwoven material.

6. The enzyme-degradable system of claim 1, wherein the outer sheets form a peripheral region.

7. The enzyme-degradable system of claim 1, further comprising at least one fastener disposed at the peripheral region of the inner and outer sheets.

8. The enzyme-degradable system of claim 1, wherein said superabsorbent polymer of the absorbent core is starch based.

9. The enzyme-degradable system of claim 1, wherein the inner sheet and the outer sheet are fabricated from a polymer blend nonwoven, or a recycled or reclaimed nonwoven material that is partially cellulose based.

10. The enzyme-degradable system of claim 1, where in the cellulase enzyme comprises a hydrolyzing enzyme.

11. An enzyme-degradable system for an undergarment and a feminine hygiene article, the system comprising:
    an absorbent core, the core including at least one of the following: a cellulose, a wood pulp, a thermoplastic aliphatic polyester, and a superabsorbent polymer;
    an inner sheet comprising a plant based cellulosic nonwoven material;

an outer sheet comprising the plant based cellulosic nonwoven material;

a cellulase enzyme being integrated into the absorbent core, or the sheets, or both, the cellulase enzyme helping to at least partially decompose at least one of: the absorbent core, the inner sheet, and the outer sheet upon contact with urine, wherein the cellulase enzyme comprises *Aspergillus niger* cellulase having an activity of 10,000-500,000 units per gram in a solid form or 10,000-500,000 units per gram in a liquid form; and at least one fastener disposed at a peripheral region of the inner and outer sheets, the fastener comprises a resilient, biodegradable material.

12. The enzyme-degradable system of claim 11, wherein the cellulase enzyme comprises a pH buffer, the pH buffer selected from one or more of the following: an inorganic phosphate, a diphosphate, a triphosphate, a pyrophosphate, an organic phosphonate, a polycarboxylic acid, a salt of sodium, potassium, calcium, sodium phosphate, sodium triphosphate, alanine, N,N-bis(carboxymethyl)-alanine, and N,N-bis(carboxymethyl)-glutamic acid.

13. The enzyme-degradable system of claim 11, wherein the cellulase enzyme comprises at least one additive, selected from: an adhesive remover, a preservative, glycerol, polyethylene glycol, an alcohol having 2-8 carbons, a sugar having 3-8 carbons, and a sugar alcohol with 3-8 carbons.

14. The enzyme-degradable system of claim 11, wherein the cellulase enzyme comprises a hydrolyzing enzyme.

\* \* \* \* \*